United States Patent [19]

Wang et al.

[11] Patent Number: 5,731,463
[45] Date of Patent: Mar. 24, 1998

[54] SELECTIVE ALKYLATION OF AN ALCOHOL SUBSTITUTED PHENOL COMPOUND

[75] Inventors: Xiu C. Wang, Gurnee; Ashok V. Bhatia, Libertyville; Steven Chamberlin, Waukegan; Luping Liu, Gurnee, all of Ill.

[73] Assignee: Abbott Laboratories, Abbott Park, Ill.

[21] Appl. No.: 717,381

[22] Filed: Sep. 23, 1996

[51] Int. Cl.⁶ .................................................. C07C 209/02
[52] U.S. Cl. .......................... 564/399; 564/349; 568/630; 568/631; 568/644
[58] Field of Search .................................. 568/630, 631, 568/644; 564/399, 349

[56] References Cited

U.S. PATENT DOCUMENTS 3,625,970  12/1971  Ambrus ........................ 260/310 C
4,252,984  2/1981  Manoury et al. .
4,760,182  7/1988  Ippolito et al. .
5,034,535  7/1991  Keding et al. .

FOREIGN PATENT DOCUMENTS 1265523  2/1990  Canada .

OTHER PUBLICATIONS

Organic Chemistry, Carey, Francis, McGraw Hill Book Co., pp. 608–610, 1987.

Primary Examiner—Brian M. Burn
Attorney, Agent, or Firm—Michael J. Ward

[57] ABSTRACT

The present invention relates to a process for the selective alkylation of intermediates of betaxolol.

25 Claims, No Drawings

SELECTIVE ALKYLATION OF AN ALCOHOL SUBSTITUTED PHENOL COMPOUND

FIELD OF THE INVENTION

The present invention relates to a novel process for the preparation of 1-{4-[2-(Cyclopropylmethoxy)ethyl]phenoxy}-3-isopropylamino-propane-2-ol hydrochloride by selective alkylation of an alcohol substituted phenol.

BACKGROUND OF THE INVENTION

The processes typically employed in producing 1-{4-[2-(Cyclopropylmethoxy)ethyl]phenoxy}-3-isopropylamino-propane-2-ol (Betaxolol) involved protecting the phenol functional group so that the alcohol functionality can be alkylated. The resulting protection and deprotection steps extend the length of the synthesis. Moreover, a chromatographic purification is required, resulting in lower overall yield.

U.S. Pat. No. 4,252,984 to Manoury et al., describes benzylation of the phenolic alcohol of 4-hydroxyphenethanoic acid. The ester group is then reduced to an alcohol and subsequently alkylated with (bromomethyl)cyclopropane. Debenzylation with $H_2$ in the presence of a catalyst deprotects the compound back to a phenolic intermediate. In a final step, addition of isopropylamine produces the end product, Betaxolol. A silica gel column is used to purify the compound. This process involves protection of the phenolic hydroxy group and subsequent deprotection.

U.S. Pat. No. 4,760,182 to Ippolito et al., describes a process for producing Betaxolol by converting 4-hydroxyphenethanol to a phenoxide anion with a base and then reacting the phenoxide anion with epichlorohydrin to produce 1-[4-(2-hydroxyethyl)phenoxy]-2,3-epoxypropane. 1-[4-(2-hydroxyethyl)phenoxy]-2,3-epoxypropane is reacted with a primary amine to produce an intermediate of Betaxolol. Protection and deprotection steps are also necessary to obtain the final product.

U.S. Pat. No. 5,034,535 to Keding et al., describes reacting 4-[2-methoxyethyl]phenol with (S)-5-hydroxymethyl-3-isopropyloxazolidin-2-one sulfonic acid ester to prepare an intermediate in the preparation of S-metoprolol.

The processes typically employed in producing Betaxolol involve extra protection and deprotection steps which make the reaction complicated. It is therefore advantageous and preferable to have a process from which the protection and deprotection steps have been eliminated. In addition, it would be a further advantage to have a process which produces highly pure betaxolol.

SUMMARY OF THE INVENTION

The present invention relates to the selective alkylation of an alcohol substituted phenol compound to form an ether product by addition of an alkylating agent in the presence of a strong base and a solvent.

DETAILED DISCLOSURE OF THE INVENTION

The present invention relates to the selective alkylation of an alcohol substituted phenol compound wherein an ether is obtained. The present invention provides for the selective alkylation of the alcohol substituent without protection and subsequent deprotection of the phenolic hydroxy moiety. In one embodiment of the present invention, a phenol compound containing an alcohol substituent can be selectively alkylated at the alcohol substituent position.

In the present invention, as represented in Scheme 1, a phenol compound containing an alcohol substituent, such as 4-hydroxyphenethanol (1), can be selectively alkylated via an oxygen dianion (2). Formation of the oxygen dianion (2) precludes the necessity of protecting the phenolic hydroxy. Reaction of 4-hydroxyphenethanol (1) in a solvent with a strong base produces an oxygen dianion (2) which is selectively alkylated to form 4-[(2-cyclopropylmethoxy)-ethyl]phenol (3) in the presence of suitable alkylating agents.

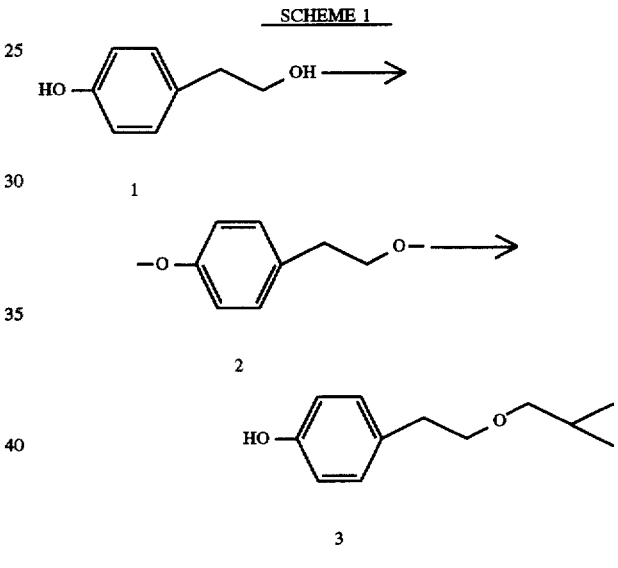

SCHEME 1

In another embodiment of the present invention, the selective alkylation process may be used in the synthesis of betaxolol intermediates. The intermediates may then be used in the synthesis of betaxolol or its salts, as shown in Scheme 2. For example, 4-[(2-cyclopropylmethoxy)-ethyl]phenol (3) may be further reacted with a halide compound, such as, but not intended to be limited to, epichlorohydrin, in the presence of base to give an epoxide, 1-{4-[2-(Cyclopropylmethoxy)-ethyl]-phenoxy}-2,3-epoxypropane (4). Subsequent addition of isopropylamine produces 1-{4-[2-(Cyclopropylmethoxy)ethyl]phenoxy}-3-isopropylamino-propane-2-ol (Betaxolol free base) which may then be converted to the hydrochloride (5) salt form by addition of HCl.

SCHEME 2

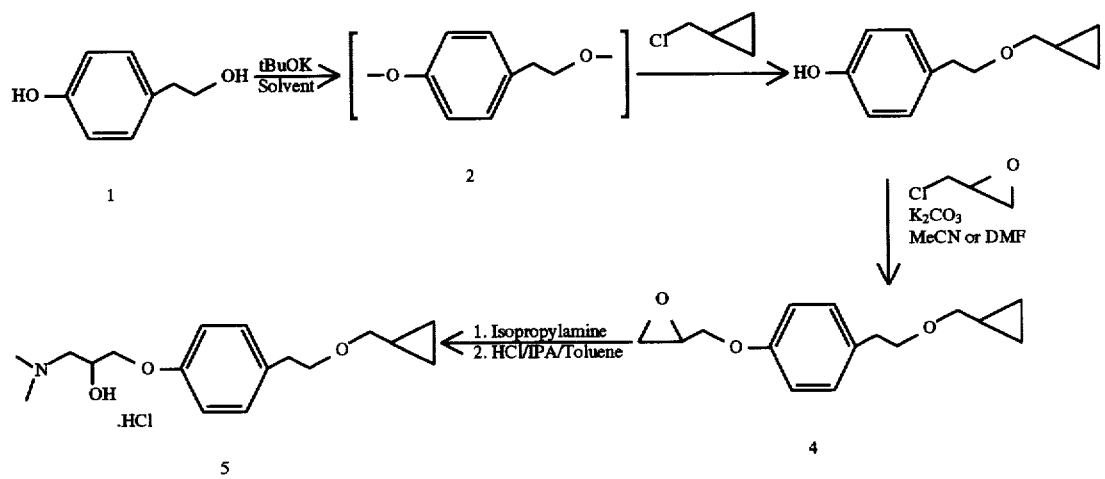

Suitable alkylating agents used in the selective alkylation of the present invention include substituted halo alkyls, halo-substituted cycloalkyls, halo-substituted cycloalkylalkyls, halo-substituted aryl alkyls, halo-substituted aryl, halo-substituted alkoxys, halo-substituted arylalkoxys, halo-substituted cycloalkoxys, halo substituted cycloalkylalkoxys, halo-substituted heterocyclics or halo-substituted (heterocyclic)alkyls. In addition, sulfonated substituted alkylating agents may be used instead of halo-substituted alkylating agents. Alkyl groups include straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like. Preferred halo alkyls include, but are not intended to be limited to, alkyl chloride, alkyl bromide, and alkyl iodide.

Suitable strong bases used in the selective alkylation of the present invention include, but are not intended to be limited to, potassium tert-butoxide, alkyllithiums including, but not limited to butyllithium (BuLi), and lithium diisopropylamide (LDA), and phenyllithium. The most preferred base is potassium tert-butoxide.

Solvents which may be used with the present invention include, but are not intended to be limited to, Dimethyl Sulfoxide, N,N-Dimethylformamide, N,N-Dimethylacetamide, 1-Methyl-2-Piperidone,1-Methyl-2-Pyrrolidone, and 1,3-Dimethyl-2-Imidazolidinone.

The temperature of the reaction is typically run at from about −10° C. to about 70° C. A more preferred temperature range is from about 0° C. to about 50° C. A most preferred temperature range is from about 20° C. to about 50° C.

The process of the present invention may be used to form salts of betaxolol. The salt forms of betaxolol may be derived from inorganic or organic acids. The salts can be prepared in situ during the final isolation and purification of the betaxolol or separately by reacting the free base of betaxolol with a suitable organic acid. These salts include but are not limited to the following: acetate, citrate, aspartate, benzoate, benzenesulfonate, bisulfate, butyrate, heptanoate, hexanoate, fumarate, hydrochloride, hydrobromide, hydroiodide, lactate, maleate, methanesulfonate, oxalate, propionate, succinate, tartate, and thiocyanate.

Examples of acids which may be employed to form acceptable salts of the compound of the present invention include such inorganic acids as hydrochloric, sulphuric, and phosphoric acids and such organic acids as acetic, oxalic, maleic, succinic, and citric acids. It is well known to one skilled in the art on how to prepare salts of betaxolol.

The following examples are intended to be illustrative of the present invention and are not to be construed as limiting.

EXAMPLE 1

4-[(2-Cyclopropylmethoxy)-ethyl]-phenol

A reaction flask was charged with 4-Hydroxyphenethyl alcohol (1) (100 g, 0.72 mol), Potassium tert-butoxide (243 g, 2.17 mol), and 500 mL of DMSO. The mixture was stirred under nitrogen at 50° C. for 30 minutes. A solution of (Chloromethyl)cyclopropane (100 g, 1.10 mol) in 500 mL of DMSO was added dropwise to the reaction mixture. The mixture was then stirred at 50° C. for one hour and then cooled to room temperature.

The reaction mixture was subsquently quenched with 1 L of water. The aqueous mixture was washed twice with 600 mL portions of toluene to remove impurities. The desired product was extracted from the neutralized aqueous mixture with toluene. The toluene extract was then washed with water and concentrated under vacuum to afford 4-[(2-Cyclopropylmethoxy)-ethyl]-phenol (3) (70.5 g, 51%).

EXAMPLE 2

1-{4-[2-(Cyclopropylmethoxy)-ethyl]-phenoxyl}-3-isopropylamino-2-ol hydrochloride (Betaxolol hydrochloride)

To a solution of 4-[(2-Cyclopropylmethoxy)-ethyl]-phenol (3) (63.02 grams, 0.328 mmol) in 600 mL of acetonitrile was added 173 grams (1.25 mmol) of potassium carbonate and 142 grams (1.53 mmol) of epichlorohydrin. After reflux for eight hours, the solids were filtered. The filtrate was concentrated by vacuum distillation. The residue was dissolved in 200 mL of toluene and the solvent was removed by vacuum distillation. The resulting residue was dissolved in 300 mL of isopropyl amine and stirred at 29°–33 ° C. for two days. Excess isopropylamine was removed under reduced presure and 300 mL of toluene was added to the residue. The product solution was extracted with 400 mL of 5% aqueous hydrochloric acid, followed by a separation of the layers. After a backwash with 300 mL of toluene, the aqueous layer was adjusted to pH 9–10 and the product was extracted with 3×300 mL of toluene. The combined toluene layers were washed twice with 300 mL portions of water. After removing toluene; by vacuum distillation, the residue was redissolved in 150 mL of toluene. To the above toluene solution, 38 mL of 36% aqueous hydrochloric acid was added and stirred at room temperature for 10 minutes. The solvent was removed by vacuum distillation, the residue was crystallized from 200 mL of acetonitrile, and then recrystallized from 350 mL of isopropanol to afford 52.6 (47% yield) grams of 1-{4-[2-(Cyclopropylmethoxy)-ethyl]-phenoxyl}-3-isopropylamino-2-ol (Betaxolol) hydrochloride with >99% purity.

I claim:

1. A process for the selective alkylation of an alcohol functionality on an alcohol substituted phenol compound comprising reacting an alkylating agent with said alcohol substituted phenol compound in the presence of a strong base and a solvent.

2. A process of claim 1 wherein said alkylating agent is selected from the group consisting of: haloalkyls, halo-substituted cycloalkyls, halo-substituted cycloalkylalkyls, halo-substituted arylalkyls, halo-substituted aryl, halo-substituted alkoxys, halo-substituted arylalkoxys, halo-substituted cycloalkoxys, halo-substituted cycloalkylalkoxys, halo-substituted heterocyclics, and halo-substituted (heterocyclic)alkyls.

3. A process of claim 1 wherein said alkylating agent is selected from the group consisting of: sulfonate substituted alkyls, cycloalkyls, cycloalkylalkyls, arylalkyls, alkoxies, arylalkoxies, cycloalkoxies, cycloalkylalkoxies, heterocyclics, and halo-substituted (heterocyclic)alkyls.

4. A process of claim 1 wherein said strong base is selected from the group consisting of: potassium tert-butoxide, alkyllithium, lithium diisopropylamide, phenyllithium, and Grignard reagents.

5. A process of claim 1 wherein the temperature of the reaction is carried out at a temperature from about −10° C. to about 70° C.

6. A process of claim 1 wherein the temperature of the reaction is carried out at a temperature from about 0° C. to about 50° C.

7. A process of claim 1 wherein the temperature of the reaction is carried out at a temperature from about 20° C. to about 50° C.

8. A process of claim 1 wherein said solvent is selected from the group consisting of: Dimethyl Sulfoxide, N,N-Dimethylformamide, N,N-Dimethylacetamide, 1-Methyl-2-Piperidone, 1-Methyl-2-Pyrrolidone, and 1,3-Dimethyl-2-Imidazolidinone.

9. A process for the production of 4-[(2-Cyclopropylmethoxy)-ethyl]-phenol comprising reacting 4-Hydroxyphenethanol with an alkyating agent in the presence of a strong base and a solvent to produce 4-[(2-Cyclopropylmethoxy)-ethyl]-phenol.

10. A process of claim 9 wherein said alkylating agent is selected from the group consisting of: haloalkyls, halo-substituted cycloalkyls, halo-substituted cycloalkylalkyls, halo-substituted arylalkyls, halo-substituted aryl, halo-substituted alkoxies, halo-substituted arylalkoxies, halo-substituted cycloalkoxies, halo-substituted cycloalkylalkoxies, halo-substituted heterocyclics, and halo-substituted (heterocyclic)alkyls.

11. A process of claim 9 wherein said alkylating agent is selected from the group consisting of: sulfonate substituted alkyls, cycloalkyls, cycloalkylalkyls, arylalkyls, alkoxys, arylalkoxys, cycloalkoxys, cycloalkylalkoxys, heterocyclics, and halo-substituted (heterocyclic)alkyls.

12. A process of claim 9 wherein said strong base is selected from the group consisting of: potassium tert-butoxide, alkyllithium, lithium diisopropylamide, phenyllithium, and Grignard reagents.

13. A process of claim 9 wherein the temperature of the reaction is carried out at a temperature from about −10° C. to about 70° C.

14. A process of claim 9 wherein the temperature of the reaction is carried out at a temperature from about 0° C. to about 50° C.

15. A process of claim 9 wherein the temperature of the reaction is carried out at a temperature from about 20° C. to about 50° C.

16. A process of claim 9 wherein said solvent is selected from the group consisting of: Dimethyl Sulfoxide, N,N-Dimethylformamide, N,N-Dimethylacetamide, 1-Methyl-2-Piperidone, 1-Methyl-2-Pyrrolidone, and 1,3-Dimethyl-2-Imidazolidinone.

17. A process of claim 9 wherein said alkyalting agent is selected from the group of (Chloromethyl)cyclopropane or (Bromomethyl)cyclopropane.

18. A process for the production of Betaxolol comprising the steps of:
   a) reacting 4-Hydroxyphenethanol with (Chloromethyl)cyclopropane or (Bromomethyl)cyclopropane in the presence of a strong base and a solvent to produce 4-[(2-Cyclopropylmethoxy)-ethyl]-phenol;
   b) reaction 4-[(2-Cyclopropylmethoxy)-ethyl]-phenol with epichlorohydrin in presence of base to form 1-{4-[2-(Cyclopropylmethoxy)-ethyl]-phenoxy}-2,3-epoxypropane; and
   c) reacting 1-{4-[2-(Cyclopropylmethoxy)ethyl]phenoxy}-2,3-epoxypropane with isopropylamine to produce Betaxolol.

19. A process of claim 18 wherein said strong base is selected from the group consisting of: potassium tert-butoxide, alkyllithium, lithium diisopropylamide, phenyllithium, and Grignard reagents.

20. A process of claim 18 wherein the temperature of the reaction is carried out at a temperature from about −10° C. to about 70° C.

21. A process of claim 18 wherein said solvent is selected from the group consisting of: Dimethyl Sulfoxide, N,N-Dimethylformamide, N,N-Dimethylacetamide, 1-Methyl-2-Piperidone, 1-Methyl-2-Pyrrolidone, and 1,3-Dimethyl-2-Imidazolidinone.

22. A process for the production of Betaxolol hydrochloride comprising the steps of:
   a) reacting 4-Hydroxyphenethanol with (Chloromethyl)cyclopropane or (Bromomethyl)cyclopropane in the presence of a strong base and a solvent to produce 4-[(2-Cyclopropylmethoxy)-ethyl]-phenol;
   b) reaction 4-[(2-Cyclopropylmethoxy)-ethyl]-phenol with epichlorohydrin in presence of base to form 1-{4-[2-(Cyclopropylmethoxy)-ethyl]-phenoxy}-2,3-epoxypropane;
   c) reacting 1-{4-[2-(Cyclopropylmethoxy)ethyl]phenoxy}-2,3-epoxypropane with isopropylamine to produce Betaxolol; and
   d) forming the hydrochloride salt form of betaxolol by addition of HCl.

23. A process of claim 22 wherein said strong base is selected from the group consisting of: potassium tert-butoxide, alkyllithium, lithium diisopropylamide, phenyllithium, and Grignard reagents.

24. A process of claim 22 wherein the temperature of the reaction is carried out at a temperature from about −10° C. to about 70° C.

25. A process of claim 22 wherein said solvent is selected from the group consisting of: Dimethyl Sulfoxide, N,N-Dimethylformamide, N,N- Dimethylacetamide, 1-Methyl-2-Piperidone, 1-Methyl-2-Pyrrolidone, and 1,3-Dimethyl-2-Imidazolidinone.

* * * * *

UNITED STATES PATENT AND TRADEMARK OFFICE
CERTIFICATE OF CORRECTION

PATENT NO. : 5,731,463
DATED : March 24, 1998
INVENTOR(S) : Wang et al.

It is certified that error appears in the above-identified patent and that said Letters Patent is hereby corrected as shown below:

Scheme 1
Column 2, line 40, change " 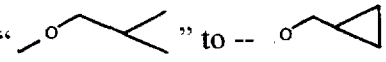 " to --  --.

Signed and Sealed this

Sixteenth Day of March, 1999

Attest:

Q. TODD DICKINSON

*Attesting Officer*   *Acting Commissioner of Patents and Trademarks*